(12) United States Patent
Whitham et al.

(10) Patent No.: US 6,465,957 B1
(45) Date of Patent: Oct. 15, 2002

(54) STANDING WAVE LINEAR ACCELERATOR WITH INTEGRAL PREBUNCHING SECTION

(75) Inventors: Kenneth Whitham, Alamo; Chong-Guo Yao, Pacheco, both of CA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 0 days.

(21) Appl. No.: 09/866,275

(22) Filed: May 25, 2001

(51) Int. Cl.[7] .............................. H01J 25/10; A61N 5/10
(52) U.S. Cl. .......................................... 315/5.41; 378/65
(58) Field of Search ................................ 315/500, 505, 315/506, 507, 5.41, 5.42; 378/65, 46, 156, 161; 313/359.1

(56) References Cited

U.S. PATENT DOCUMENTS

| | | |
|---|---|---|
| 3,456,207 A | 7/1969 | Badger |
| 3,811,065 A | 5/1974 | Lien |
| 3,942,066 A | 3/1976 | Kageyama et al. |
| 3,953,758 A | 4/1976 | Tran |
| 4,006,422 A | 2/1977 | Schriber |
| 4,024,426 A | 5/1977 | Vaguine |
| 4,027,193 A | 5/1977 | Schriber |
| 4,118,653 A | 10/1978 | Vaguine |
| 4,160,189 A | 7/1979 | Tran et al. |
| 4,162,423 A | 7/1979 | Tran |
| 4,400,650 A | 8/1983 | Giebeler, Jr. |
| 4,629,938 A * | 12/1986 | Whitham .................... 315/5.41 |
| 4,641,103 A | 2/1987 | Madey et al. |
| 4,988,919 A * | 1/1991 | Tanabe et al. ............. 315/5.41 |
| 5,321,271 A | 6/1994 | Schonberg et al. |
| 5,418,372 A | 5/1995 | Schonberg et al. |
| 6,316,876 B1 * | 11/2001 | Tanabe ........................ 315/5.41 |
| 6,366,641 B1 * | 4/2002 | Whitham ..................... 378/65 |
| 6,376,990 B1 * | 4/2002 | Allen et al. ................ 315/5.41 |

* cited by examiner

*Primary Examiner*—Don Wong
*Assistant Examiner*—Minh D A

(57) ABSTRACT

A standing wave linear accelerator with a prebunching section and an accelerating section that are formed into a unitary accelerating structure is described. The prebunching section is configured to group charged particles into bunches by velocity modulation of the charged particle beam. The accelerating section has a plurality of inter-coupled resonant cavities, including an input cavity that is coupled to the prebunching section and an output cavity.

20 Claims, 2 Drawing Sheets

STANDING WAVE LINEAR ACCELERATOR WITH INTEGRAL PREBUNCHING SECTION

TECHNICAL FIELD

This invention relates to standing wave linear accelerators and, in particular, relates to standing wave linear accelerators for use in medical radiotherapy systems.

BACKGROUND

Radiation therapy involves delivering a high, curative dose of radiation to a tumor, while minimizing the dose delivered to surrounding healthy tissues and adjacent healthy organs. Therapeutic radiation doses may be supplied by a standing wave linear accelerator that is configured to generate a high-energy (e.g., several MeV) electron beam. In an electron mode of operation, the electron beam may be applied directly to one or more therapy sites on a patient. Alternatively, in a radiation mode of operation, the electron beam may be used to generate a photon (e.g., X-ray) beam that may be applied to the patient. The shape of the radiation beam at the therapy site may be controlled by discrete collimators of various shapes and sizes or by multiple leaves (or finger projections) of a multi-leaf collimator that are positioned to block selected portions of the radiation beam. In this way, the radiation beam may be contained within the boundaries of the therapy site, whereby healthy tissues and organs that are located beyond the boundaries of the therapy site may be protected against exposure to the radiation beam.

In general, a standing wave linear accelerator includes a particle source (e.g., an electron gun) that directs charged particles (e.g., electrons) into an accelerating cavity. The charged particles travel through a succession of accelerating cavities, in which the particles are focused and accelerated by an electromagnetic (RF) field that is applied by an external RF source (e.g., a klystron amplifier or a magnetron oscillator). The charged particles typically are formed and compacted into bunches by the initial accelerating cavities that are traversed by the charged particle beam. Bunching the charged particles increases the number of electrons available for acceleration at the fundamental resonant frequency of the accelerating cavities. This feature allows the charged particle source to operate at lower power levels and improves the overall efficiency of the system.

SUMMARY

The invention features a standing wave linear accelerator with a prebunching section and an accelerating section that are formed into a unitary accelerating structure. The prebunching section is configured to group charged particles into bunches by velocity modulation of the charged particle beam. The accelerating section has a plurality of inter-coupled resonant cavities, including an input cavity that is coupled to the prebunching section and an output cavity.

Embodiments in accordance with this aspect of the invention may include one or more of the following features.

The prebunching section of the unitary accelerating structure preferably is configured to group charged particles into bunches without net charged particle acceleration.

The accelerating section of the unitary accelerating structure preferably incorporates a bunching section for accelerating and further grouping charged particle bunches that are received from the prebunching section. The accelerating section of the unitary accelerating structure may be characterized by a fundamental resonant frequency, and the bunching section may be configured to further group charged particle bunches that are received from the prebunching section for more efficient modulation at the fundamental resonant frequency.

The system may include a power coupling circuit that is configured to enable independent phase and amplitude adjustment of rf energy that is injected into the prebunching and accelerating sections of the unitary accelerating structure. The prebunching and accelerating sections of the unitary accelerating structure may be coupled to the same source of rf energy. A directional coupler may be configured to apportion rf energy from the rf source between the prebunching section and the accelerating section.

In one embodiment, the prebunching section of the unitary accelerating structure includes a single resonant cavity. The resonant cavities of the accelerating section may be inter-coupled by side cavities.

A drift tube may be formed between the prebunching and accelerating sections of the unitary accelerating structure. A charged particle source may be coupled to the prebunching section of the unitary accelerating structure. In some embodiments, the charged particle source is a low-voltage electron gun.

In another aspect, the invention features a system for generating a therapeutic beam that includes a charged particle source, a standing wave linear accelerator that is formed from the above-described unitary accelerating structure, and a system that is configured to shape the therapeutic beam for delivery to a therapy site on a patient.

In some embodiments in accordance with this aspect of the invention, an x-ray target positioned to intercept a charged particle beam that is accelerated by the standing wave linear accelerator.

Among the advantages of the invention are the following.

In accordance with the invention, the reliability and operating efficiency of the linear accelerator are improved by forming the prebunching section integrally with the accelerating section. For example, such an integrated structure reduces concentration of electric fields at the interface between the prebunching section and the accelerating section that otherwise might limit the maximum power level at which the accelerator may be operated. In addition, such an integrated structure allows the accelerator to be manufactured more quickly and more cost effectively than if the prebunching section were formed as a separate unit and merely bolted or otherwise not integrally attached to the accelerating section.

Other features and advantages of the invention will become apparent from the following description, including the drawings and the claims.

DETAILED DESCRIPTION

In the following description, like reference numbers are used to identify like elements. Furthermore, the drawings are intended to illustrate major features of exemplary embodiments in a diagrammatic manner. The drawings are not intended to depict every feature of actual embodiments nor relative dimensions of the depicted elements, and are not drawn to scale.

Figure 1:
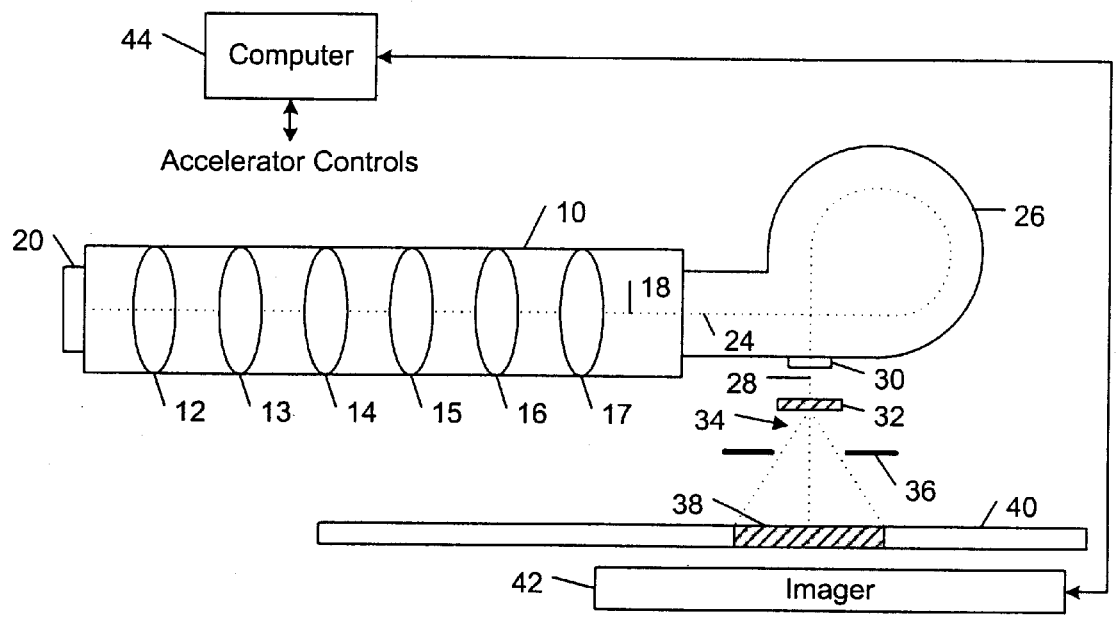
FIG. 1 is a block diagram of a radiation treatment system delivering a therapeutic radiation beam to a therapy site on a patient.

Referring to FIG. 1, in one embodiment, a standing wave charged particle linear accelerator 10 for use in a medical radiotherapy system includes a series of accelerating cavities 12, 13, 14, 15, 16, 17 that are aligned along a beam axis 18. A particle source 20 (e.g., an electron gun) directs charged particles (e.g., electrons) into the input accelerating cavity 12. As the charged particles travel through the succession of accelerating cavities 12–17, the particles are focused and accelerated by an electromagnetic field that is applied by an external source (e.g., a magnetron oscillator or a klystron amplifier). The resulting accelerated particle beam 24 may be directed to a magnetic energy filter 26 that bends beam 24 by approximately 270°. A filtered output beam 28 is directed through a window 30 to a target 32 that generates an x-ray beam 34. The intensity of radiation beam 34 typically is constant. One or more adjustable leaves 36 may be positioned to block selected portions of radiation beam 34 to conform the boundary of radiation beam 34 to the boundaries of a therapy site 38 on a patient 40. An imager 42 collects image data corresponding to the intensity of radiation passing through patient 40. A computer 44 typically is programmed to control the operation of leaves 36 to generate a prescribed intensity profile over the course of a treatment, and to control the operation of linear accelerator 10 and imager 42.

Figure 2:
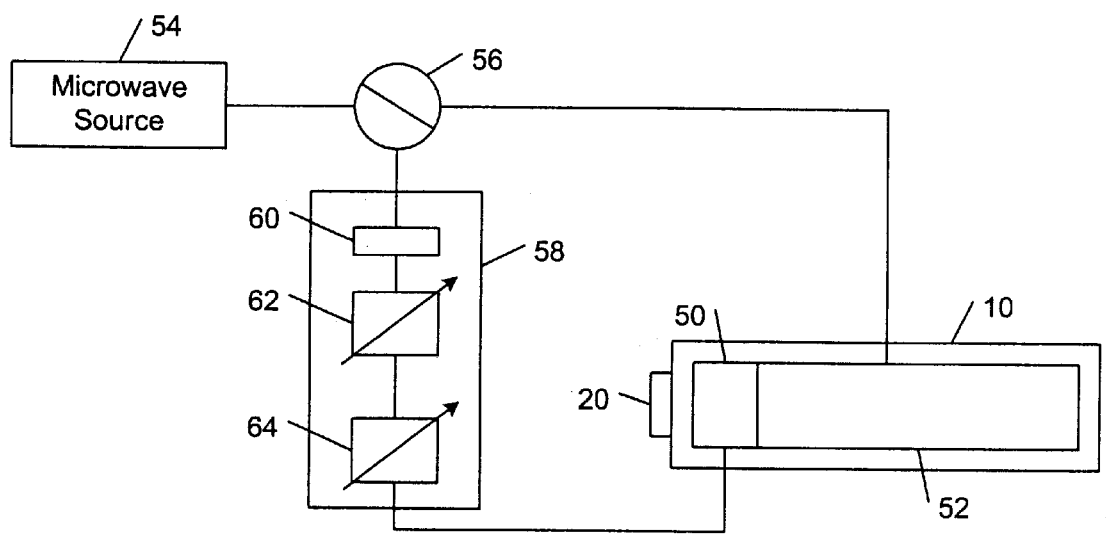
FIG. 2 is a block diagram of a microwave power supply system coupled to a standing wave linear accelerator with an integral prebunching section.

As shown in FIG. 2, standing wave linear accelerator 10 is a unitary structure that includes a prebunching section 50 and an accelerating section 52. Prebunching section 50 is configured to group charged particles into bunches by velocity modulation of the charge particle beam that is injected by particle source 20. The velocity modulation is converted into a density modulation in a drift tube that is coupled between the prebunching and accelerating sections 50, 52 of linear accelerator 10. In addition to accelerating the prebunched charge particle beam, the initial cavities of accelerating section 52 further bunch the charged particle beam. The resulting charged particle beam is bunched into a very short phase spread at the front end of the accelerator to provide high beam capture efficiency and maintain small energy spread in the accelerated output beam 24.

Prebunching section 50 and accelerating section 52 are driven by the same microwave power source 54 (e.g., a magnetron oscillator or a klystron amplifier). However, as explained in detail below, the amplitude and phase of the rf energy supplied to prebunching section 50 may be controlled independently of the phase and amplitude of the rf energy supplied to accelerating section 52. A directional coupler 56 diverts a portion of the rf energy generated by microwave source 54 to a power coupling circuit 58, which is coupled to prebunching section 50; the remaining output rf energy is diverted to accelerating section 52. Typically, directional coupler 56 diverts on the order of 1 kW of input power to prebunching section 50 and allows on the order of about 1 MW of input power to be supplied to accelerating section 52. Power coupling circuit 58 includes an isolator 60, a variable attenuator 62 and a variable phase shifter 64, which are coupled in series. Isolator 60 reduces wave reflections caused by impedance mismatches between the power transmission system and the components of linear accelerator 10. Variable attenuator 62 enables the energy supplied to prebunching section 50 to be varied over a wide range of values so that the charged particle bunch density may be optimized. Phase shifter 64 enables the phase of the rf wave generated inside prebunching section 50 to be adjusted relative to the phase of the standing wave inside accelerating section 52 so that the energy of the accelerated output beam 24 may be selectively varied. By this arrangement, linear accelerator 10 may be operated at different power levels without a broadening of the output energy spectrum and without a decrease in capture efficiency.

In operation, prebunching section 50 modulates the phase and amplitude of the charged particles so that the particles become grouped into bunches without net acceleration. The electron distribution within each bunch may be substantially uniform and the velocity spread may be negligible. In this way, a high capture efficiency and a narrow energy spectrum in the output beam 24 may be achieved. The resonant standing wave microwave fields induced inside accelerating section 52 accelerate the prebunched charged particles essentially to the velocity of light. As described above, the resulting charged particle beam 24 may bombard an x-ray target to produce high energy x-rays, or may irradiate patient 40 or another object directly.

Figure 3:
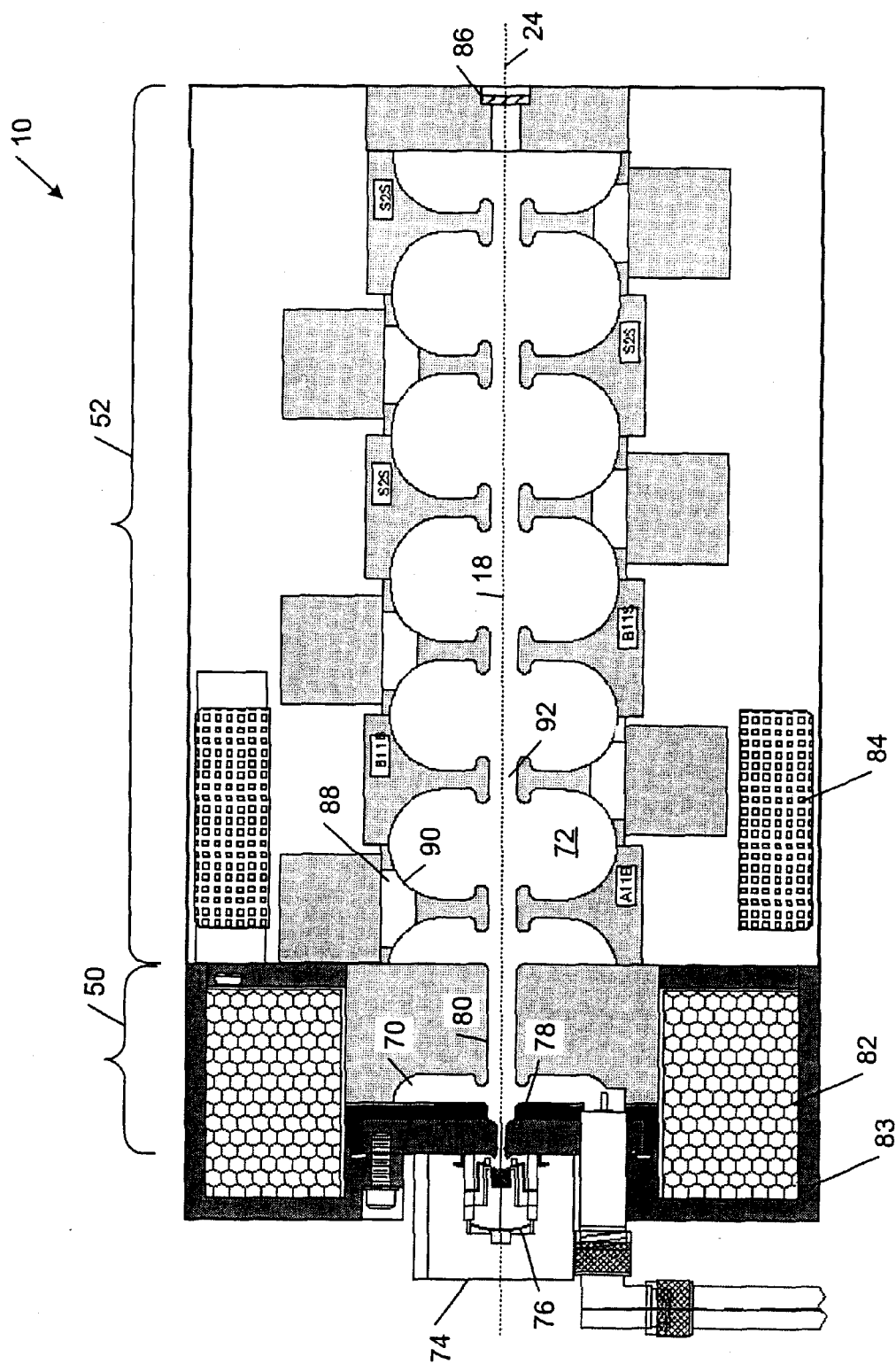
FIG. 3 is a diagrammatic cross-sectional side view of a side cavity coupled standing wave linear accelerator with an integral prebunching section.

Referring to FIG. 3, in one embodiment, linear accelerator 10 has a prebunching section 50 with a single prebunching cavity 70 having a Q-factor that is, for example, on the order of 1,000, and an accelerating section 52 with a plurality of inter-coupled, high-Q resonant accelerating cavities 72. Accelerating cavities 72 are arranged successively along beam axis 18 and are configured to accelerate charged particles to nearly the velocity of light. The prebunching section 50 and the accelerating section 52 may be formed from copper assemblies that are brazed together to form a unitary accelerating structure. An electron gun 74 is coupled to prebunching section 50. Electron gun 74 includes an injector cathode 76 and an anode plug 78 that are configured to inject electrons into prebunching cavity 70. A drift tube 80 is coupled between prebunching cavity 70 and the input cavity of accelerating section 52. A pair of solenoids (or focusing coils) 82, 84 are disposed around prebunching cavity 70 and the initial accelerating cavities of accelerating section 52 and are configured to generate magnetic fields for confining the electron beam and for improving the electron beam transmission efficiency of the unitary structure. A magnetic stainless steel enclosure 83 surrounds solenoid 82. An output window 86, which is disposed at the downstream end of linear accelerator 10, is permeable to the high energy output particle beam 24, but is impermeable to gas molecules. In operation, linear accelerator 10 and electron gun 74 typically are evacuated to a suitably low pressure (e.g., $10^{-6}$ torr) by a vacuum pump (not shown).

Accelerating section 52 also includes a plurality of coupling cavities 88 that are disposed off beam axis 18 and are configured to couple adjacent accelerating cavities 72 electromagnetically. Each coupling cavity 88 is disposed tangentially to the accelerating cavities 72. The corners of each coupling cavity 88 intersect the inside walls of a pair of adjacent accelerating cavities 72 to define magnetic field coupling irises 90, which provide electromagnetic wave energy coupling between the accelerating cavities 72 and the associated coupling cavities 88. The accelerating cavities 72 and the coupling cavities 88 are tuned substantially to the same frequency.

In one mode of operation, the gaps 92 between accelerating cavities 72 are spaced so that charged particles travel from one gap to the next in ½ rf cycle of the microwave source. As a result, after experiencing an accelerating field in one gap, the charged particles arrive at the next gap when the direction of the field in the next gap has reversed direction to further accelerate the charged particles. The field in each side cavity 88 is advanced in phase by $\pi/2$ radians from the preceding accelerating cavity 72 so that the complete resonant structure of accelerating section 52 operates in a mode with $\pi/2$ phase shift per cavity (i.e., a $\pi/2$ resonance mode). Since charged particle beam does not interact with side cavities 88, the charged particle beam experiences the equivalent acceleration of a structure with a $\pi$-radian phase shift between adjacent accelerating cavities 72. In this embodiment, the essentially standing wave pattern that is induced within linear accelerator has very small fields in side cavities 88 because the end cavities also are configured as accelerating cavities 72. This feature minimizes rf losses in the non-working side cavities 88. In addition, configuring the end cavities as half cavities improves the charged particle beam entrance conditions and provides a symmetrical resonant structure with uniform fields in each accelerating cavity 72. In one embodiment, the microwave source 54 is configured for S-band operation, and the cavity resonators 72 in accelerating section 52 are configured to be resonant at S-band. In one embodiment, the microwave source 54 may provide sufficient energy for linear accelerator 10 to produce a charged particle beam 24 with a maximum output energy in the range of about 4 MeV to about 24 MeV, while operating in a $\pi/2$ resonance mode.

Linear accelerator 10 also may be operated in a number of different, non-$\pi/2$ resonance (or standing wave) modes.

Other embodiments are within the scope of the claims.

For example, although the above embodiments are described in connection with side coupling cavities, other forms of energy coupling (e.g., coupling cavities pancaked between accelerating cavities 72) may be used.

In some embodiments, prebunching section 50 may include more than one prebunching cavity.

Still other embodiments are within the scope of the claims.

What is claimed is:

1. A system for accelerating a charged particle beam, comprising:
    a unitary accelerating structure having a prebunching section configured to group charged particles into bunches by velocity modulation of the charged particle beam and an accelerating section with a plurality of inter-coupled resonant cavities including an input cavity coupled to the prebunching section and an output cavity.

2. The system of claim 1, wherein the prebunching section of the unitary accelerating structure is configured to group charged particles into bunches without net charged particle acceleration.

3. The system of claim 1, wherein the accelerating section of the unitary accelerating structure incorporates a bunching section for accelerating and further grouping charged particle bunches received from the prebunching section.

4. The system of claim 3, wherein the accelerating section of the unitary accelerating structure is characterized by a fundamental resonant frequency, and the bunching section is configured to further group charged particle bunches received from the prebunching section for more efficient modulation at the fundamental resonant frequency.

5. The system of claim 1, further comprising a power coupling circuit configured to enable independent phase and amplitude adjustment of rf energy injected into the prebunching and accelerating sections of the unitary accelerating structure.

6. The system of claim 1, wherein the prebunching and accelerating sections of the unitary accelerating structure are coupled to the same source of rf energy.

7. The system of claim 6, further comprising a directional coupler configured to apportion rf energy from the rf source between the prebunching section and the accelerating section.

8. The system of claim 1, further comprising a drift tube formed between the prebunching and accelerating sections of the unitary accelerating structure.

9. The system of claim 1, wherein the prebunching section includes a single resonant cavity.

10. The system of claim 1, wherein the resonant cavities of the accelerating section of the unitary accelerating structure are inter-coupled by side cavities.

11. The system of claim 1, further comprising a charged particle source coupled to the prebunching section of the unitary accelerating structure.

12. The system of claim 11, wherein the charged particle source is a low-voltage electron gun.

13. A system for generating a therapeutic beam, comprising:
    a charged particle source;
    a standing wave linear accelerator formed from a unitary accelerating structure having a prebunching section coupled to the charged particle source and configured to group charged particles into bunches by velocity modulation of the charged particle beam, and an accelerating section with a plurality of intercoupled resonant cavities including an input cavity coupled to the prebunching section and an output cavity; and
    a system configured to shape the therapeutic beam for delivery to a therapy site on a patient.

14. The system of claim 13, further comprising an x-ray target positioned to intercept a charged particle beam accelerated by the standing wave linear accelerator.

15. The system of claim 13, wherein the prebunching section of the unitary accelerating structure is configured to group charged particles into bunches without net charged particle acceleration.

16. The system of claim 13, wherein the accelerating section of the unitary accelerating structure incorporates a bunching section for accelerating and further grouping charged particle bunches received from the prebunching section.

17. The system of claim 16, wherein the accelerating section of the unitary accelerating structure is characterized by a fundamental resonant frequency, and the bunching section is configured to further group charged particle bunches received from the prebunching section for more efficient modulation at the fundamental resonant frequency.

18. The system of claim 13, further comprising a power coupling circuit configured to enable independent phase and amplitude adjustment of rf energy injected into the prebunching and accelerating sections of the unitary accelerating structure.

19. The system of claim 13, wherein the prebunching and accelerating sections of the unitary accelerating structure are coupled to the same source of rf energy.

20. The system of claim 19, further comprising a directional coupler configured to apportion rf energy from the rf source between the prebunching section and the accelerating section.

* * * * *